(12) United States Patent
Merritt et al.

(10) Patent No.: US 9,974,443 B2
(45) Date of Patent: *May 22, 2018

(54) DEVICES, SYSTEMS, AND METHODS AND ASSOCIATED DISPLAY SCREENS FOR ASSESSMENT OF VESSELS

(71) Applicant: KONINKLIJKE PHILIPS N.V., Eindhoven (NL)

(72) Inventors: Fergus Merritt, Escondido, CA (US); Vaishali Mittal, Folsom, CA (US)

(73) Assignee: Koninklijke Philips N.V., Eindhoven (NL)

(*) Notice: Subject to any disclaimer, the term of this patent is extended or adjusted under 35 U.S.C. 154(b) by 440 days.

This patent is subject to a terminal disclaimer.

(21) Appl. No.: 14/627,441

(22) Filed: Feb. 20, 2015

(65) Prior Publication Data

US 2015/0230713 A1 Aug. 20, 2015

Related U.S. Application Data

(60) Provisional application No. 61/942,338, filed on Feb. 20, 2014, provisional application No. 61/943,168, filed on Feb. 21, 2014.

(51) Int. Cl.
*A61B 5/02* (2006.01)
*A61B 5/0215* (2006.01)
*A61B 5/00* (2006.01)

(52) U.S. Cl.
CPC ...... *A61B 5/02007* (2013.01); *A61B 5/02158* (2013.01); *A61B 5/7278* (2013.01);
(Continued)

(58) Field of Classification Search
CPC ............ A61B 5/02152; A61B 5/02158; A61B 5/02155
See application file for complete search history.

(56) References Cited

U.S. PATENT DOCUMENTS 6,193,669 B1 * 2/2001 Degany ............ A61B 5/02014
600/486
6,354,999 B1 3/2002 Dgany et al.
(Continued)

FOREIGN PATENT DOCUMENTS

EP 2298162 3/2011
WO WO 00-53081 A1 9/2000
(Continued)

OTHER PUBLICATIONS

WO2013/028612 (PCT/US2012/051566) International Preliminary Report on Patentability issued by International Bureau of WIPO dated Feb. 25, 2014, 1 page.
(Continued)

*Primary Examiner* — Christian Jang

(57) ABSTRACT

Devices, systems, and methods for visually depicting a vessel and evaluating treatment options are disclosed. The methods can include obtaining pressure measurements from first and second instruments positioned within a vessel of a patient while the second instrument is moved longitudinally through the vessel from a first position to a second position and the first instrument remains stationary within the vessel; and outputting a visual representation of the pressure measurements obtained by the first and second instruments on a display, the output visual representation including a graphical display of a pressure ratio of the obtained pressure measurements and at least a portion of a pressure waveform of the obtained pressure measurements identifying a diagnostic period utilized in calculating the pressure ratio.

14 Claims, 10 Drawing Sheets

(52) U.S. Cl.
CPC .............. *A61B 5/742* (2013.01); *A61B 5/743* (2013.01); *A61B 5/02152* (2013.01); *A61B 5/748* (2013.01)

(56) References Cited

U.S. PATENT DOCUMENTS

| | | |
|---|---|---|
| 2006/0052700 A1 | 3/2006 | Svanerudh |
| 2006/0106321 A1 | 5/2006 | Lewinsky et al. |
| 2007/0060822 A1 | 3/2007 | Alpert et al. |
| 2008/0139951 A1 | 6/2008 | Patangay et al. |
| 2010/0234698 A1 | 9/2010 | Manstrom et al. |
| 2013/0046190 A1 | 2/2013 | Davies |
| 2015/0025330 A1 | 1/2015 | Davies et al. |
| 2015/0025398 A1 | 1/2015 | Davies et al. |

FOREIGN PATENT DOCUMENTS

| | | |
|---|---|---|
| WO | WO 01-13779 A2 | 3/2001 |
| WO | WO 2013/028612 | 2/2012 |
| WO | WO 2012/093260 | 7/2012 |
| WO | WO 2012/093266 | 7/2012 |

OTHER PUBLICATIONS

WO2013/028612 (PCT/US2012/051566) International Search Report and Written Opinion issued by International Bureau of WIPO dated Mar. 29, 2013, 9 pages.
WO2013/093260 (PCT/GB2012/050015) International Preliminary Report on Patentability issued by International Bureau of WIPO dated Jul. 10, 2013, 1 page.
WO2013/093260 (PCT/GB2012/050015) International Search Report and Written Opinion issued by International Bureau of WIPO dated Apr. 20, 2012, 14 pages.
WO 2012/093266 (PCT/GB2012/050024) International Preliminary Report on Patentability issued by International Bureau of WIPO dated Jul. 10, 2013, 1 page.
WO 2012/093266 (PCT/GB2012/050024) International Search Report and Written Opinion issued by International Bureau of WIPO dated Apr. 19, 2012, 15 pages.
J.E. Davies, Evidence of a Dominant Backward-Propagating "Suction" Wave Responsible for Diastolic Coronary Filling in Humans, Attenuated in Left Ventricular Hypertrophy, Circulation, vol. 113, No. 14, Apr. 11, 2006, pp. 1768-1778.

* cited by examiner

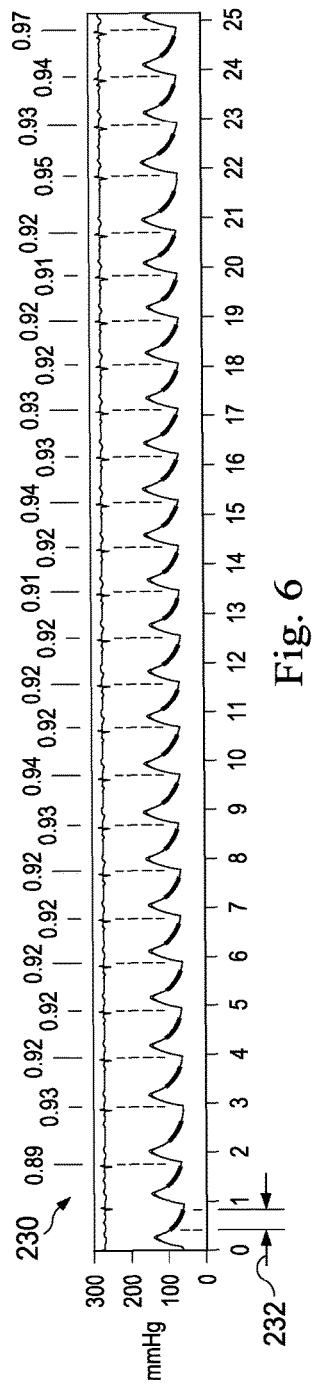
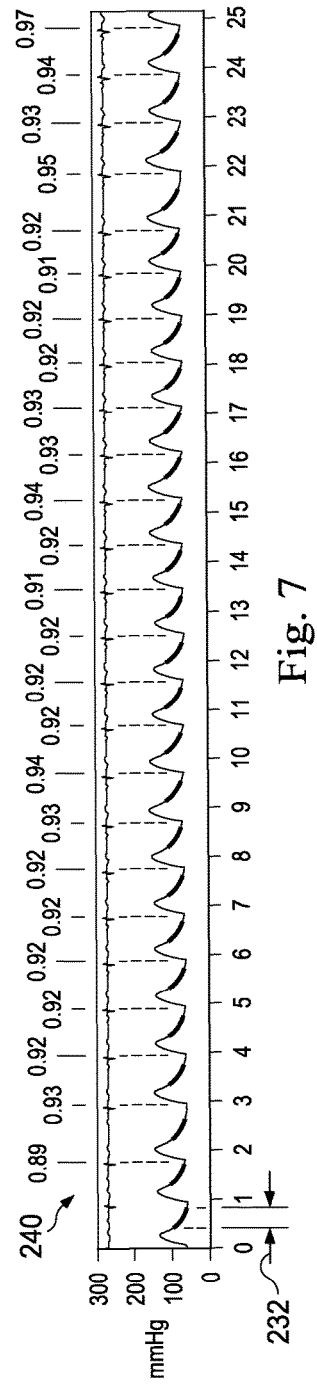
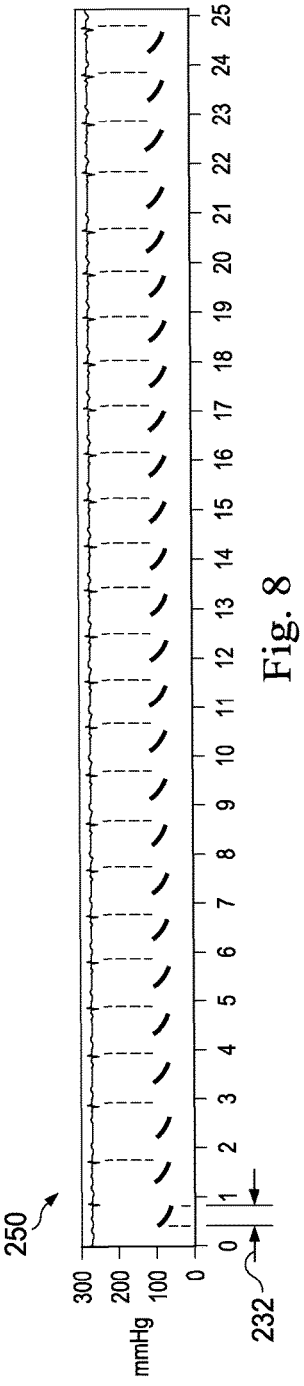
Fig. 6
Fig. 7
Fig. 8

DEVICES, SYSTEMS, AND METHODS AND ASSOCIATED DISPLAY SCREENS FOR ASSESSMENT OF VESSELS

CROSS REFERENCE TO RELATED APPLICATIONS

The present application claims priority to and the benefit of the U.S. Provisional Patent Application Nos. 61/942,338, filed Feb. 20, 2014 and 61/943,168, filed Feb. 21, 2014, which are hereby incorporated by reference in their entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance predominantly by reducing the microcirculation resistance associated with the systolic portion of the heart cycle to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents. Further, there remains a need for improved devices, systems, and methods for providing visual depictions of vessel that allow assessment of the vessel and, in particular, any stenosis or lesion of the vessel.

SUMMARY

Embodiments of the present disclosure are configured to assess the severity of a blockage in a vessel and, in particular, a stenosis in a blood vessel. In some particular embodiments, the devices, systems, and methods of the present disclosure are configured to provide screen displays that allow assessment of the vessel and, in particular, any stenosis or lesion of the vessel.

In some embodiments, methods of evaluating a vessel of a patient are provided. The method includes obtaining pressure measurements from first and second instruments positioned within a vessel of a patient while the second instrument is moved longitudinally through the vessel from a first position to a second position and the first instrument remains stationary within the vessel; and outputting a visual representation of the pressure measurements obtained by the first and second instruments on a display, the output visual representation including a graphical display of a pressure ratio of the obtained pressure measurements and at least a portion of a pressure waveform of the obtained pressure measurements identifying a diagnostic period utilized in calculating the pressure ratio. In some implementations, the first position is distal of at least one stenosis of the vessel and the second position is proximal of the at least one stenosis of the vessel such that moving the second instrument longitudinally through the vessel comprises a pullback. In some instances, the graphical display of the pressure ratio of the obtained pressure measurements includes a numerical value of the pressure ratio. In some instances, the graphical display of the pressure ratio of the obtained pressure measurements includes a graph of the pressure ratio. In other instances, the graphical display of the pressure ratio of the obtained pressure measurements includes a graph of a change in the pressure ratio. In other instances, the graphical display of the pressure ratio of the obtained pressure measurements includes separate plots of the pressure measurements obtained with the first instrument and the pressure measurements obtained with the second instrument. In some instances, the screen display further includes a graph of a difference in the pressure measurements obtained with the first instrument and the pressure measurements obtained with the second instrument.

A system for evaluating a vessel of a patient is also provided that includes a first instrument sized and shaped for introduction into the vessel of the patient; a second instrument sized and shaped for introduction into the vessel of the patient; a processing system in communication with the first and second instruments, the processing unit configured to: obtain pressure measurements from the first and second instruments while the second instrument is moved longitudinally through the vessel of the patient from a first position to a second position while the first instrument is maintained in a fixed longitudinal position with respect to the vessel; and output a screen display having visual representations of the pressure measurements obtained by the first and second instruments on a display in communication with the processing system, the screen display including: a graphical display of a pressure ratio of the obtained pressure measurements; and at least a portion of a pressure waveform of the obtained pressure measurements identifying a diagnostic period utilized in calculating the pressure ratio.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 6 shows a portion of a screen display according to another embodiment of the present disclosure.

FIG. 7 shows a portion of a screen display according to another embodiment of the present disclosure.

FIG. 8 shows a portion of a screen display according to another embodiment of the present disclosure.

DETAILED DESCRIPTION

Figure 1:
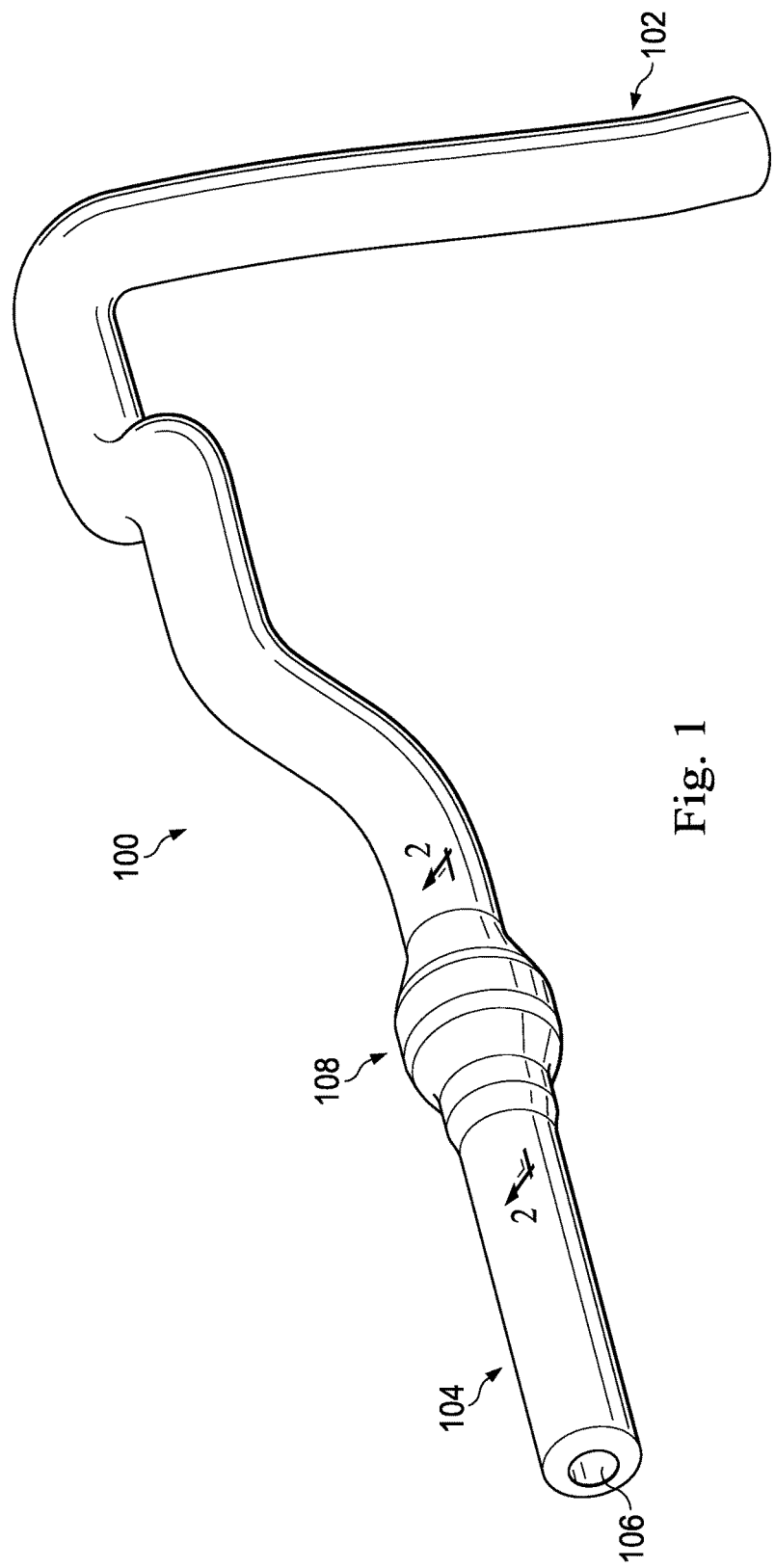
FIG. 1 shows a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
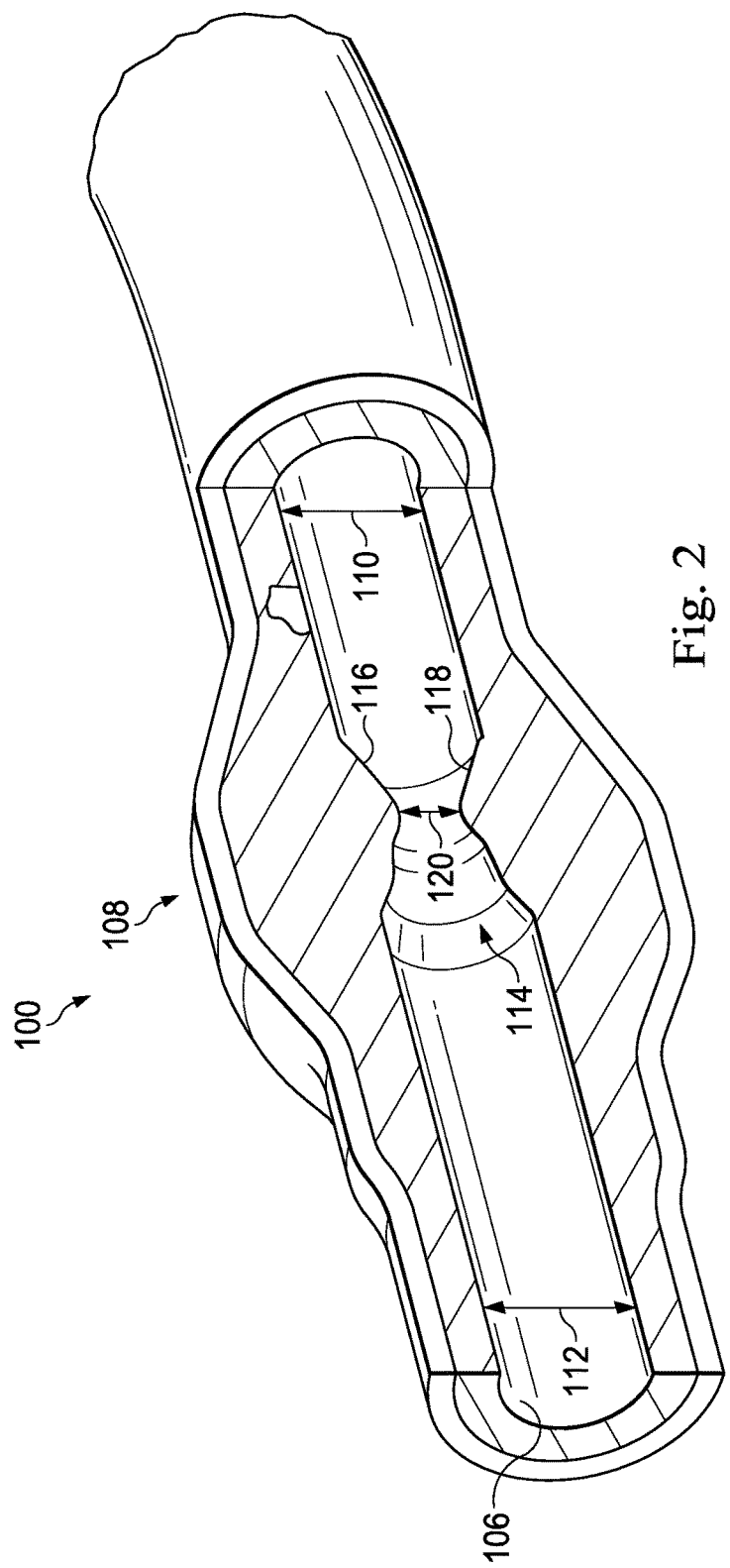
FIG. 2 shows a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
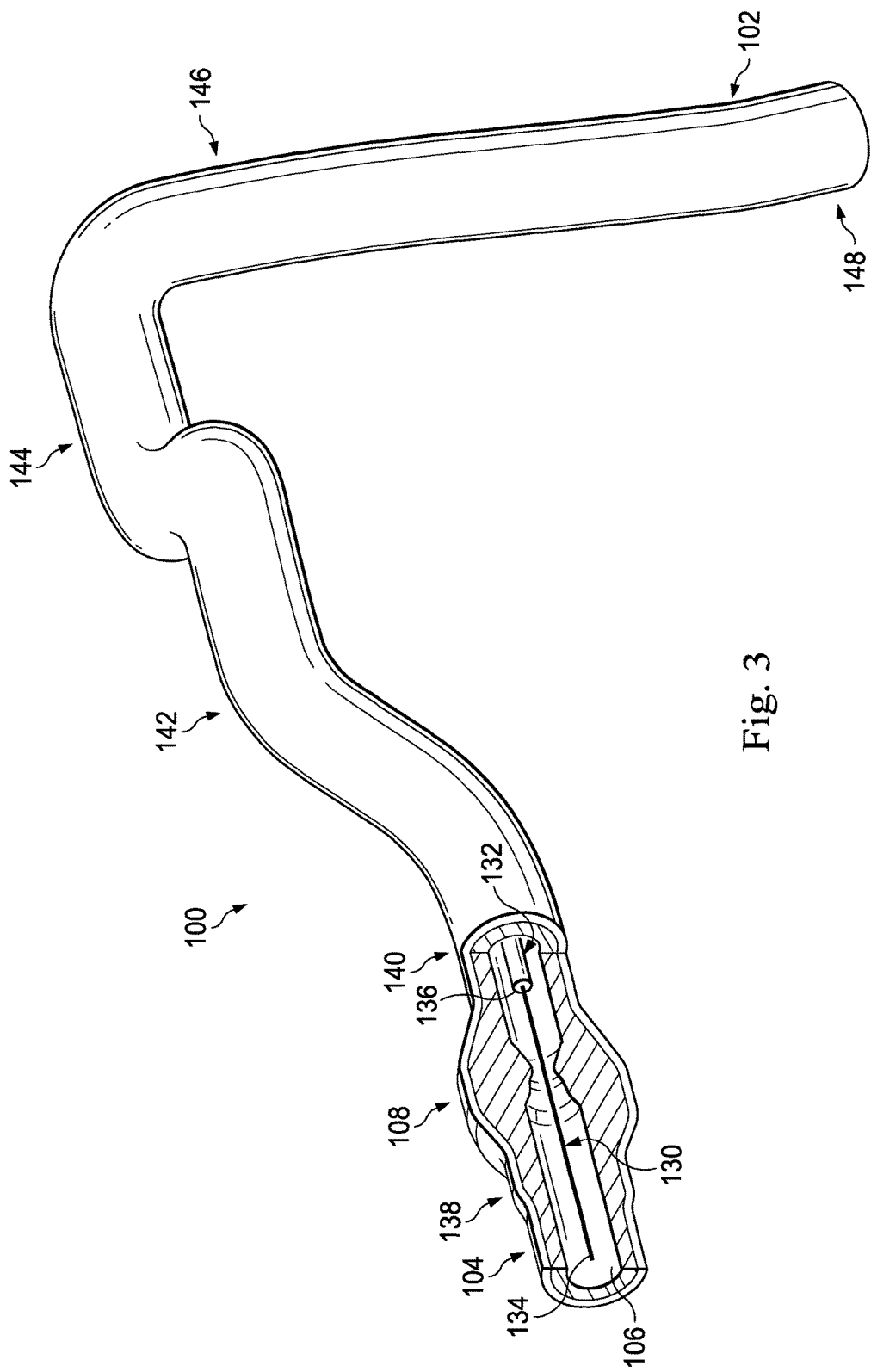
FIG. 3 shows a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guide wire relative to the pressure reading of a guide catheter. In that regard, because FFR is calculated as the ratio of the pressure measurement obtained by the guide wire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 4:
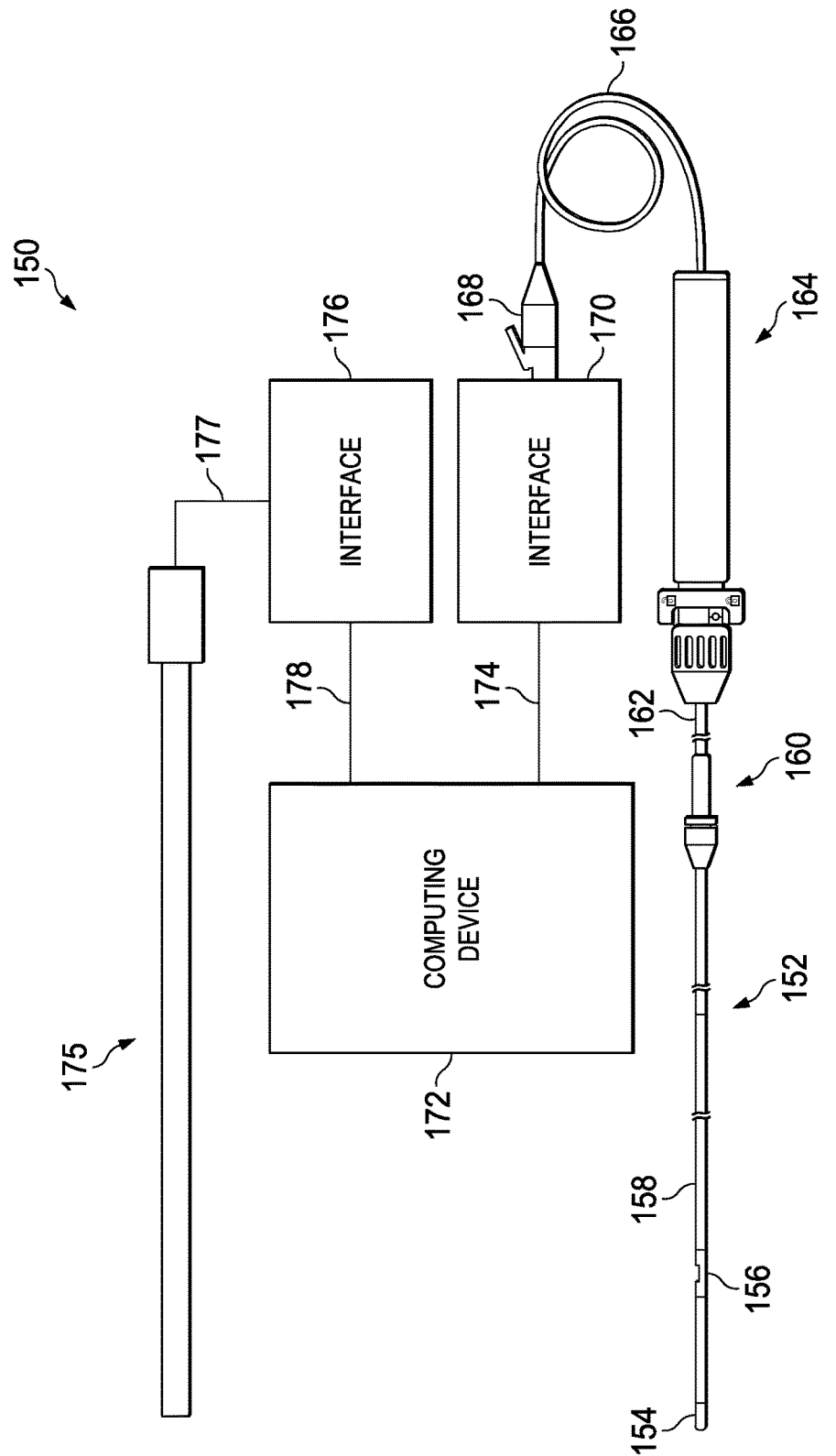
FIG. 4 shows a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
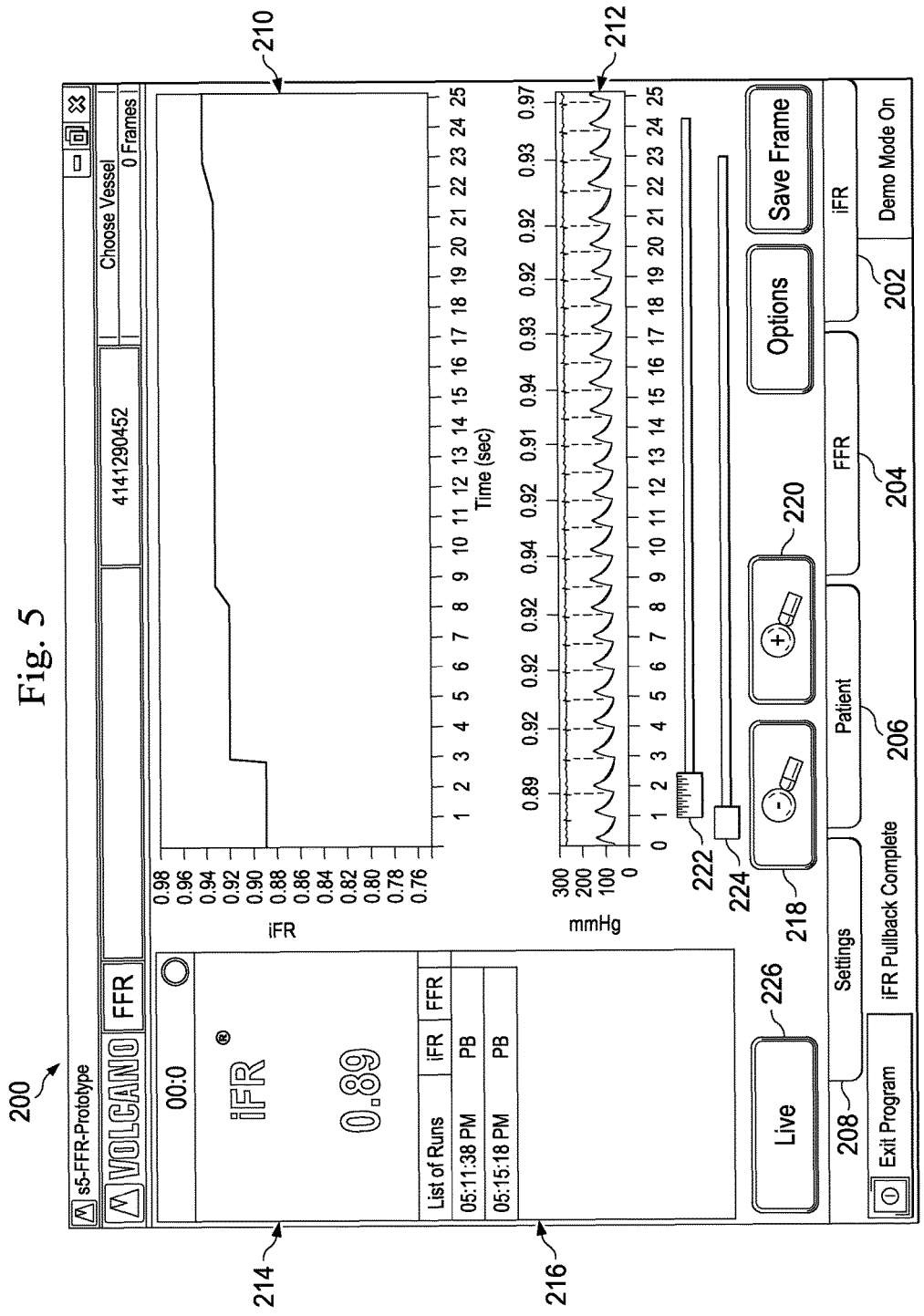
FIG. 5 shows a screen display according to an embodiment of the present disclosure.

Referring now to FIGS. 5-12, shown therein are various visual depictions of screen displays for evaluating a vessel based on obtained pressure measurements according to embodiments of the present disclosure. Referring more specifically to FIG. 5, shown therein is a screen display 200 according to an embodiment of the present disclosure. The screen display 200 includes multiple tabs, including an iFR tab 202, an FFR tab 204, a patient tab 206, and a settings tab 208. In FIG. 5, the iFR tab 202 has been selected and displayed to a user. As shown, the iFR tab 202 includes a graph 210 and a corresponding a pressure waveform plot 212. The screen display 200 also includes a window 214 that shows a calculated pressure ratio (e.g., FFR, iFR, or otherwise). The screen display 200 also includes a window 216 showing the runs or pullbacks available for display to the user. In the illustrated embodiment, two different runs are available and identified by a corresponding time stamp. In that regard, a user can select the desired run from the window 216 and the data shown in the graph 210 and pressure waveform plot 212 will update accordingly.

The screen display 200 also includes zoom buttons 218, 220 that allow a user to zoom out or in, respectively, on the graph 210 and the pressure waveform plot 212. To this end, the screen display 200 includes a ruler 222 showing the relative scale of the graph 210 and the pressure waveform plot 212. In some instances, the ruler 222 provides a dimensional scale of the graphical display of the graph 210 and/or the pressure waveform plot 212 relative to the vessel length and/or the pullback length. The scale of the ruler 222 automatically updates in response to selective actuation of the zoom buttons 218, 220 in some implementations.

The screen display 200 also includes a slider 224. The slider 224 allows the user to move along the length of the vessel and/or the corresponding pullback data. For example, in some instances the left end of the slider 224 corresponds to the beginning of the pullback and the right end of the slider corresponds to the end of the pullback. By moving the slider 224 between the first and second ends, a user can see corresponding portions of the pressure data in the graph 210 and the pressure waveform plot 212. Accordingly, a user can focus on certain portions of the vessel and pullback data using the zoom buttons 218, 220 in combination with the slider 224. In some instances, the numerical value of the pressure ratio displayed in window 214 is updated based on the position of the slider and/or. In that regard, in some instances the numerical value of the pressure ratio displayed in window 214 is based solely on the pressure data being displayed in the graph 210 and the pressure waveform plot 212. However, in other instances the numerical value of the pressure ratio displayed in window 214 is based one of or a combination of the pressure data being displayed in the graph 210 and the pressure waveform plot 212 and pressure data not displayed in the graph 210 and the pressure waveform plot 212.

In that regard, the graph 210 and pressure waveform plot 212 of screen display 200 illustrate aspects of pressure measurements obtained as one instrument is moved through the vessel and another instrument is maintained at a fixed location. In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, published as U.S. Patent Application Publication No. 2013/0046190 on Feb. 21, 2013 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In the illustrated embodiment of FIG. 5, the graph 210 shows the pressure ratio over time. In particular, the graph 210 shows the pressure ratio calculated over the time of a pullback. More specifically, the graph 210 shows an iFR pressure ratio value during a pullback. In that regard, the iFR pressure ratio may be calculated as described in one or more of PCT Patent Application Publication No. WO 2012/093260, filed Jan. 6, 2012 and titled "APPARATUS AND METHOD OF CHARACTERISING A NARROWING IN A FLUID FILLED TUBE," PCT Patent Application Publication No. WO 2012/093266, filed Jan. 6, 2012 and titled "APPARATUS AND METHOD OF ASSESSING A NARROWING IN A FLUID FILLED TUBE," U.S. patent application Ser. No. 13/460,296, published as U.S. Patent Application Publication No. 2013/0046190 on Feb. 21, 2013 and titled "DEVICES, SYSTEMS, AND METHODS FOR ASSESSING A VESSEL," PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. patent application Ser. No. 14/335,603, published as U.S. Patent Application Publication No. 2015/0025330 on Jan. 22, 2015 and titled "DEVICES, SYSTEMS, AND METHODS FOR ASSESSMENT OF VESSELS," and U.S. patent application Ser. No. 14/335,680, published as U.S. Patent Application Publication No. 2015/0025398 on Jan. 22, 2015 and titled "DEVICES, SYSTEMS, AND METHODS FOR ASSESSING A VESSEL WITH AUTOMATED DRIFT CORRECTION," each of which is hereby incorporated by reference in its entirety.

The graph 210 can illustrate the pressure ratio and/or the underlying pressure measurements in any suitable way. In that regard, FIGS. 9-12 described below illustrate various exemplary embodiments. Generally speaking, the representation of the data in graph 210 can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

Likewise, the pressure waveform plot 212 shows the corresponding pressure data. In that regard, the pressure waveform plot 212 can include the pressure waveform for the pressure sensing device moved through the vessel during the pullback, the pressure waveform for the stationary pressure sensing device, or both. In the illustrated embodiment, the pressure waveform plot 212 includes the pressure waveforms for both. As will be discussed below with respect to FIGS. 6-8, in some instances the pressure waveform plot 212 is augmented to highlight or otherwise accentuate the pressure data corresponding to the diagnostic window utilized for the pressure ratio calculations.

As shown in FIG. 5, the screen display 200 includes a button 226 indicating that the data is being displayed in a "Live" mode, which indicates that the screen display 200, including graph 210, pressure waveform plot 212, and/or the window 214, is being updated in real time as a procedure is being performed. In other instances, the button 226 of the screen display 200 will indicated that it is in "Playback" or "Review" mode, which indicates that the screen display 200 is showing data obtained previously. With respect to the "Live" mode, it should be noted that the determination of the diagnostic window and/or the calculation of the pressure differential are performed in approximately real time or live to identify the diagnostic window of the heartbeat cycle and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the pressure differential measurements depicted in graph 210 and/or window 214 of the screen display 200 of FIG. 5 are configured based on the threshold value in some instances. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). Further, in some instances the graph 210 includes one or more horizontal lines or other depictions representing the threshold value(s). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

Referring now to FIGS. 6-8, shown therein are various displays of pressure waveform plots according to the present disclosure. In particular, the embodiments of FIGS. 6-8 may be used in place of the pressure waveform plot 212 in any of the screen displays of the present disclosure. To that end, the pressure waveform plots of FIGS. 6-8 highlight, emphasis, and/or otherwise accentuate the portion(s) of the pressure data utilized in making the pressure ratio calculations depicted in the other graphs and/or windows of the screen displays. In particular, in some implementations the pressure waveform plots of FIGS. 6-8 identify the diagnostic window utilized in making iFR calculations.

Referring more specifically to FIG. 6, shown therein is a pressure waveform plot 230 that corresponds to the same data as shown in pressure waveform plot 212 of FIG. 5, but where the pressure data for each heartbeat that is within the diagnostic window utilized for making the iFR calculations shown in graph 210 and window 214 has been highlighted. For example, for the first heartbeat cycle on the left side of the pressure waveform plot 230, the pressure data within a diagnostic window 232 has been highlighted. By highlighting the portions of the pressure waveform plot 230 within the diagnostic window for each heartbeat cycle, a user can quickly visualize the pressure data being relied upon for the resulting pressure ratio calculations.

FIGS. 7 and 8 illustrate other ways of identifying the portions of the pressure waveform plot within the diagnostic window for each heartbeat cycle. For example, FIG. 7 shows a pressure waveform plot 240 that corresponds to the same data as shown in pressure waveform plots 212 and 230 above, but where the pressure data for each heartbeat that is within the diagnostic window utilized for making the iFR calculations shown in graph 210 and window 214 has been highlighted and the pressure data for each heartbeat that is outside of the diagnostic window has been faded. In particular, for the first heartbeat cycle on the left side of the pressure waveform plot 240, the pressure data within the diagnostic window 232 has been highlighted and the remaining pressure data for the first heartbeat cycle is shown in faded or other low contrast setting. Similarly, FIG. 8 shows a pressure waveform plot 250 that corresponds to the same data as shown in pressure waveform plots 212, 230, and 240 above, but where the pressure data for each heartbeat that is within the diagnostic window utilized for making the iFR calculations shown in graph 210 and window 214 has been highlighted and the pressure data for each heartbeat that is outside of the diagnostic window has been removed entirely. In particular, for the first heartbeat cycle on the left side of the pressure waveform plot 250, the pressure data within the diagnostic window 232 has been highlighted and the remaining pressure data for the first heartbeat cycle has been removed. Accordingly, the pressure waveform plot 250 only shows the pressure data within the diagnostic window 232. It is understood that the pressure data within the diagnostic window can be identified and/or accentuated in any suitable manner.

Figure 9:
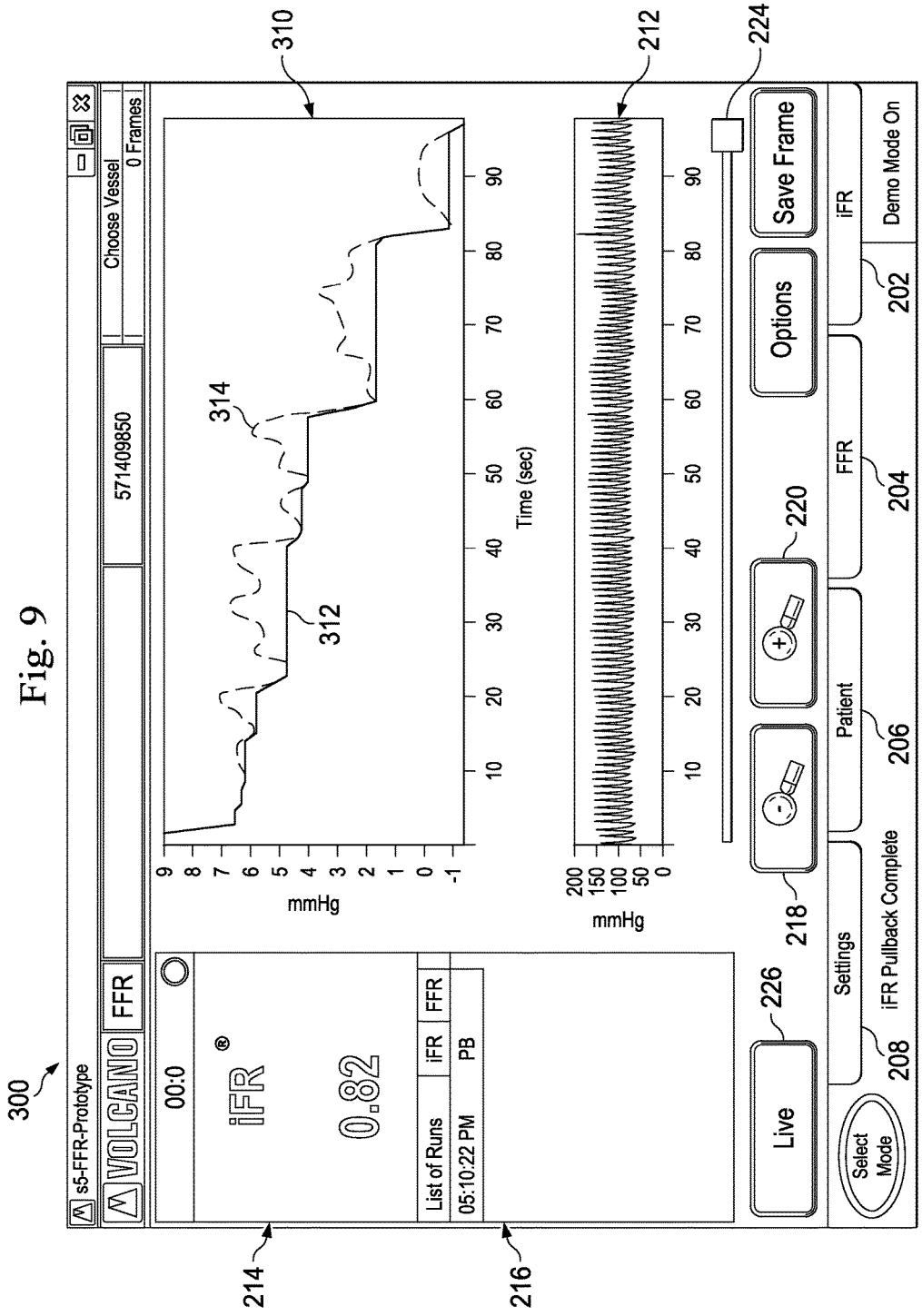
FIG. 9 shows a screen display according to an embodiment of the present disclosure.

Referring now to FIG. 9, shown therein is a screen display 300 according to another embodiment of the present disclosure. The screen display 300 is similar in many respects to screen display 200 described above. However, the screen display 300 includes a graph 310 that shows a pressure difference during a pullback, instead of an iFR value over time of the pullback (as shown in graph 210 of screen display 200). In particular, the graph 310 includes a plot 312 that represents the difference in pressure between the instrument maintained at a fixed location (for sake of brevity, this will be referred to as Pa below) and the instrument moved through the vessel for the pullback over time (for sake of brevity, this will be referred to as Pd below). In some implementations, the difference in pressure is calculated as follows, $\Delta P = Pa - Pd$, for each heartbeat cycle. In some instances, the difference in pressure may be referred to as the pressure gradient. In that regard, a mean, median, mode, and/or other suitable value (e.g., filtering to remove outliers, then using mean, median, and/or mode, etc.) is calculated and utilized for each of Pa and Pd for each heartbeat cycle. In that regard, in some instances the mean, median, mode, and/or other suitable value used to represent Pa and/or Pd for each heartbeat cycle is calculated using the pressure data within the diagnostic window(s) for each heartbeat cycle (as highlighted in FIGS. 6-8).

The graph 310 also includes a plot 314 that is shown in a faded or phantom manner. In some implementations the plot 314 represents raw iFR data, while the plot 312 represents conditioned and/or filtered iFR data. In that regard, due to various reasons (noise, interference, physiological effects (e.g., patient movement, coughing, irregular heartbeat, etc.), and/or other disruptions in the pressure measurements) the raw iFR data may include variations that are not realistically representative of actual changes in iFR values during a pullback. Accordingly, in some instances the raw iFR data of plot 314 is smoothed, filtered, conditioned, and/or otherwise treated to remove abnormalities in the iFR values. For example, plot 312 has been constrained such that the pressure differences are equal to or less than the pressure differences for positions more distal during the pullback and, therefore, equal to or greater than the pressure ratios for positions more proximal during the pullback. Generally, any suitable processing techniques can be utilized to adjust the values of the raw iFR data shown in plot 314 to create the conditioned iFR data of plot 312. In some instances, the Pa, Pd, and/or iFR data is conditioned, filtered, or otherwise treated as described in U.S. patent application Ser. No. 14/335,680, published as U.S. Patent Application Publication No. 2015/0025398 on Jan. 22, 2015 and titled "DEVICES, SYSTEMS, AND METHODS FOR ASSESSING A VESSEL WITH AUTOMATED DRIFT CORRECTION," which is hereby incorporated by reference in its entirety.

Figure 10:
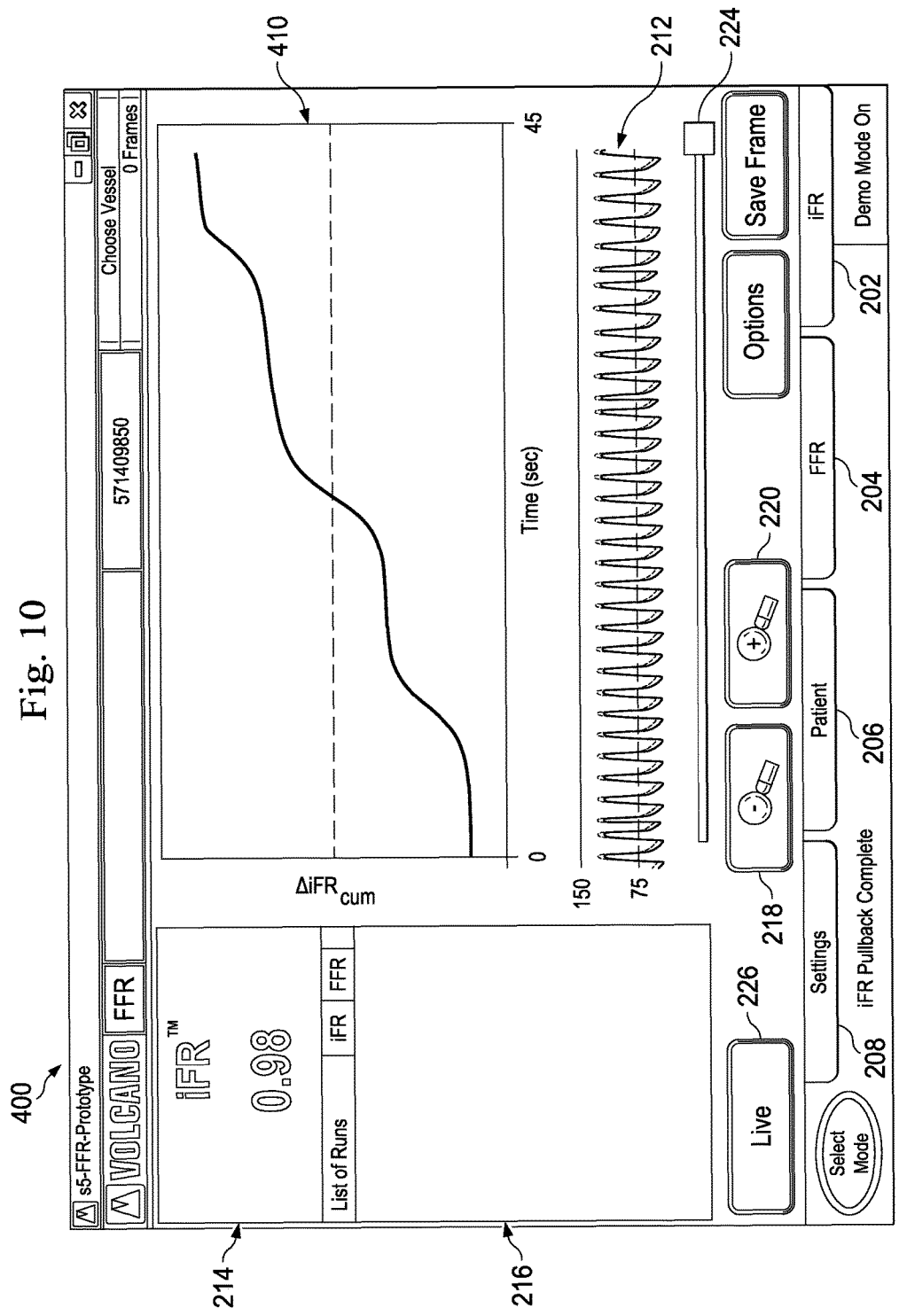
FIG. 10 shows a screen display according to an embodiment of the present disclosure.

Referring now to FIG. 10, shown therein is a screen display 400 according to another embodiment of the present disclosure. The screen display 400 is similar in many respects to screen displays 200 and 300 described above. However, the screen display 400 includes a graph 410 that shows a cumulative change in a pressure ratio value over time during a pullback. In particular, the graph 410 includes a plot that represents the cumulative change in iFR value over time. In some implementations, the cumulative change in iFR value displayed in graph 410 is calculated as follows, $\Delta iFR_{cum_n} = (iFR_n - iFR_{n+1}) + \Delta iFR_{cum_{n-1}}$. In that regard, n represents each heartbeat cycle in some implementations. In other instances, n represents a fixed amount of time or a fixed amount of pullback length. Further, a mean, median, mode, and/or other suitable value (e.g., filtering to remove outliers, then using mean, median, and/or mode, etc.) is calculated and utilized for Pa, Pd, and/or the resulting iFR values for each heartbeat cycle. In that regard, in some instances the mean, median, mode, and/or other suitable value used to represent Pa, Pd, and/or the iFR value for each heartbeat cycle is calculated based on the pressure data within the diagnostic window(s) for each heartbeat cycle (as highlighted in FIGS. 6-8). Again, the iFR value can be calculated using the techniques described in one or more of applications incorporated by reference above. By utilizing a cumulative iFR change in graph 410 the location of significant changes in iFR values, which are often associated with the presence of a lesion or stenosis, can be visually identified by a user. In addition, the relative significance of the change in iFR value to total change in iFR value along the length of the pullback can be visualized. In this way, the relative impact of the lesion or stenosis can be estimated visually.

Figure 11:
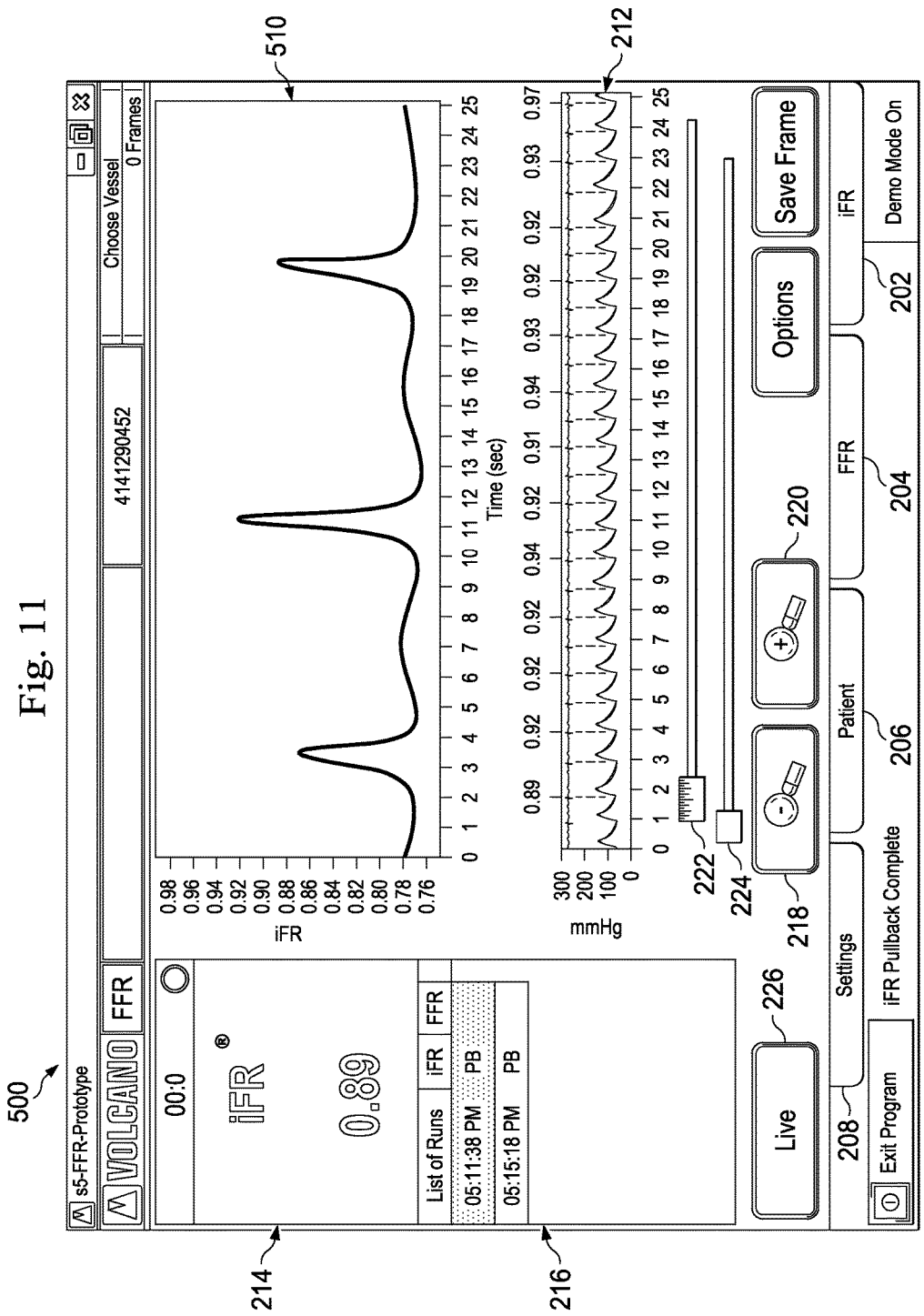
FIG. 11 shows a screen display according to an embodiment of the present disclosure.

Referring now to FIG. 11, shown therein is a screen display 500 according to another embodiment of the present disclosure. The screen display 500 is similar in many respects to screen displays 200, 300, and 400 described above. However, the screen display 500 includes a graph 510 that shows a change in a pressure ratio value over time during a pullback. In particular, the graph 510 includes a plot that represents a localized change in iFR value over time. In that regard, the localized iFR change is calculated as the difference between the immediately preceding or following point in some instances. For example, in some implementations, the change in iFR value displayed in graph 510 is calculated as follows, $\Delta iFR_n = iFR_n - iFR_{n+1}$ or $\Delta iFR_n = iFR_n - iFR_{n+1}$ In that regard, n represents each heartbeat cycle in some implementations. In other instances, n represents a fixed amount of time or a fixed amount of pullback length. Further, a mean, median, mode, and/or other suitable value (e.g., filtering to remove outliers, then using mean, median, and/or mode, etc.) is calculated and utilized for Pa, Pd, and/or the resulting iFR values for each heartbeat cycle. In that regard, in some instances the mean, median, mode, and/or other suitable value used to represent Pa, Pd, and/or the iFR value for each heartbeat cycle is calculated based on the pressure data within the diagnostic window(s) for each heartbeat cycle (as highlighted in FIGS. 6-8). Again, the iFR value can be calculated using the techniques described in one or more of applications incorporated by reference above. By utilizing a localized iFR change in graph 510 the location of significant changes in iFR values, which are often associated with the presence of a lesion or stenosis, can be visually identified by a user.

Figure 12:
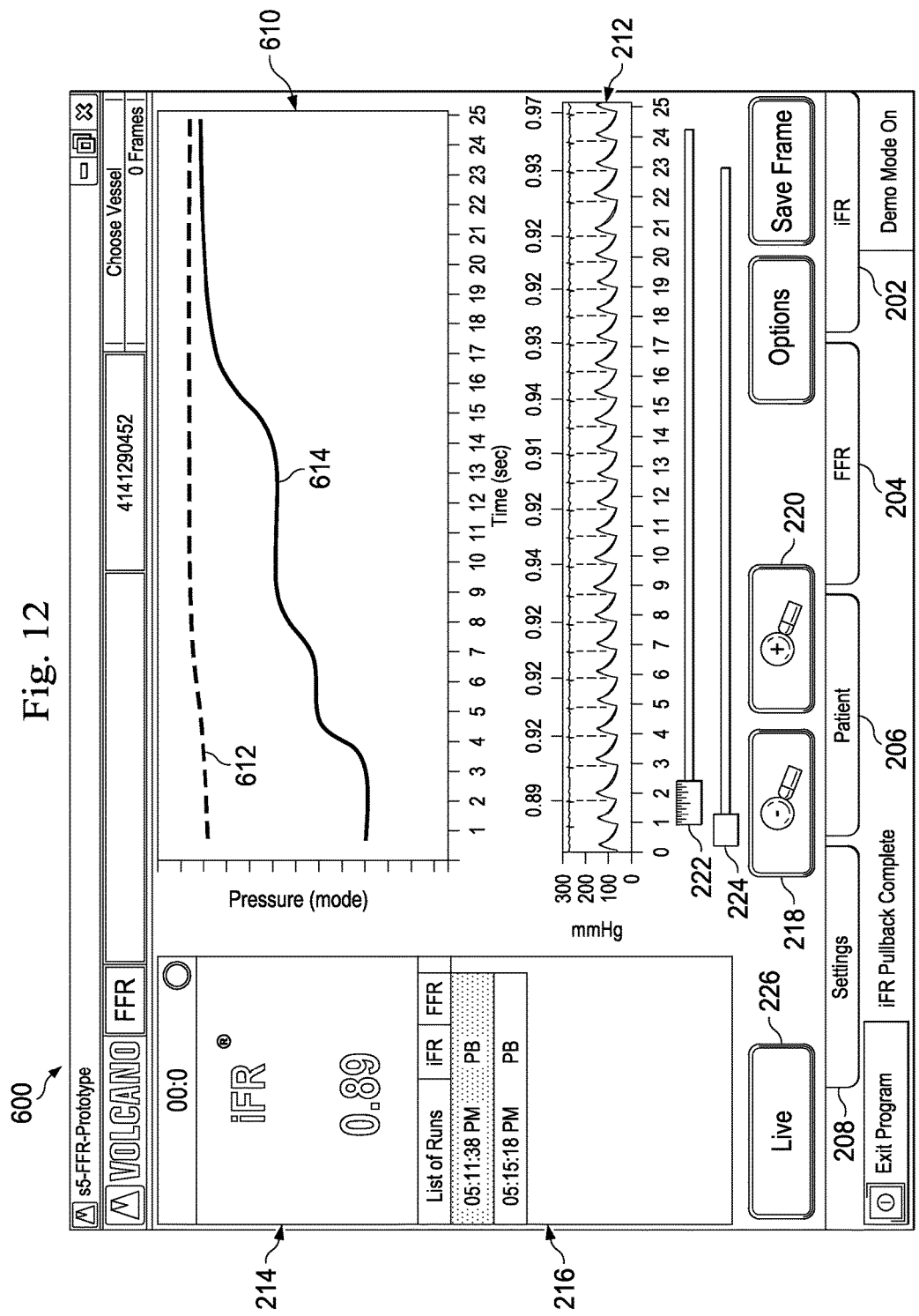
FIG. 12 shows a screen display according to an embodiment of the present disclosure.

Referring now to FIG. 12, shown therein is a screen display 600 according to another embodiment of the present disclosure. The screen display 600 is similar in many respects to screen displays 200, 300, 400, and 500 described above. However, the screen display 600 includes a graph 610 that shows Pa and Pd pressures over time during a pullback. In particular, the graph 610 includes a plot 612 that represents Pa during the pullback and a plot 614 that represents Pd during the pullback. In that regard, a mean, median, mode, and/or other suitable value (e.g., filtering to remove outliers, then using mean, median, and/or mode, etc.) is calculated and utilized for each of Pa and Pd for each heartbeat cycle. In that regard, in some instances the mean, median, mode, and/or other suitable value used to represent Pa and/or Pd for each heartbeat cycle is calculated using the pressure data within the diagnostic window(s) for each heartbeat cycle (as highlighted in FIGS. 6-8).

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:
    obtaining pressure measurements from first and second instruments positioned within a vessel of a patient while the second instrument is moved longitudinally through the vessel from a first position to a second position and the first instrument remains stationary within the vessel; and
    outputting a screen display having visual representations of a pressure ratio calculated using the pressure measurements obtained by the first and second instruments on a display, the screen display including:
    a numerical value of the pressure ratio; and
    a graph of the pressure ratio over a time the second instrument is moved longitudinally through the vessel from the first position to the second position.

2. The method of claim 1, wherein the first position is distal of at least one stenosis of the vessel and wherein the second position is proximal of the at least one stenosis of the vessel such that moving the second instrument longitudinally through the vessel comprises a pullback.

3. The method of claim 1, wherein the graph of the pressure ratio comprises a change in the pressure ratio over the time.

4. The method of claim 3, wherein the change in the pressure ratio comprises a cumulative change in the pressure ratio over the time.

5. The method of claim 3, wherein the change in the pressure ratio comprises a localized change in the pressure ratio over the time.

6. The method of claim 1, wherein screen display comprises a first area comprising the numerical value and a second area comprising the graph of the pressure ratio.

7. The method of claim 6, wherein the first area is adjacent to the second area.

8. A system for evaluating a vessel of a patient, comprising:
    a processing system in communication with first and second instruments sized and shaped for introduction into the vessel of the patient, the processing unit configured to:
    obtain pressure measurements from the first and second instruments while the second instrument is moved longitudinally through the vessel of the patient from a first position to a second position while the first instrument is maintained in a fixed longitudinal position with respect to the vessel; and
    output a screen display having visual representations of a pressure ratio calculated using the pressure measurements obtained by the first and second instruments on a display in communication with the processing system, the screen display including:

a numerical value of the pressure ratio; and
a graph of the pressure ratio over a time the second instrument is moved longitudinally through the vessel from the first position to the second position.

9. The system of claim 8, wherein the first position is distal of at least one stenosis of the vessel and wherein the second position is proximal of the at least one stenosis of the vessel such that moving the second instrument longitudinally through the vessel comprises a pullback.

10. The system of claim 8, wherein the graph of the pressure ratio comprises a change in the pressure ratio over the time.

11. The system of claim 10, wherein the change in the pressure ratio comprises a cumulative change in the pressure ratio over the time.

12. The system of claim 10, wherein the change in the pressure ratio comprises a localized change in the pressure ratio over the time.

13. The system of claim 8, wherein screen display comprises a first area comprising the numerical value and a second area comprising the graph of the pressure ratio.

14. The system of claim 13, wherein the first area is adjacent to the second area.

* * * * *